United States Patent
Wandel

[11] Patent Number: 5,807,302
[45] Date of Patent: Sep. 15, 1998

[54] TREATMENT OF GLAUCOMA

[76] Inventor: Thaddeus Wandel, 136 Old Post Rd. North, Croton, N.Y. 10520

[21] Appl. No.: 625,243

[22] Filed: Apr. 1, 1996

[51] Int. Cl.$^6$ ..................................................... A61M 5/00
[52] U.S. Cl. ................................................................ 604/8
[58] Field of Search ................................. 604/8–18, 49, 604/104, 30, 31, 34, 294

[56] References Cited

U.S. PATENT DOCUMENTS

| | | |
|---|---|---|
| 4,968,296 | 11/1990 | Ritch et al. . |
| 5,041,081 | 8/1991 | Odrich . |
| 5,092,837 | 3/1992 | Ritch et al. . |
| 5,127,901 | 7/1992 | Odrich . |
| 5,171,213 | 12/1992 | Price, Jr. . |
| 5,178,604 | 1/1993 | Baerveldt et al. . |
| 5,300,020 | 4/1994 | L'Esperance, Jr. . |
| 5,326,345 | 7/1994 | Price, Jr. . |
| 5,338,291 | 8/1994 | Speckman et al. . |
| 5,346,464 | 9/1994 | Camras . |
| 5,370,607 | 12/1994 | Memmen . |
| 5,433,701 | 7/1995 | Rubinstein . |

*Primary Examiner*—John G. Weiss
*Assistant Examiner*—Ki Yong O
*Attorney, Agent, or Firm*—Graham & James LLP

[57] ABSTRACT

A treatment of glaucoma by direct flow of the aqueous humor through a slit passage in the cornea to the tear film, while maintaining sterility of the anterior chamber. A stent device, supported by the cornea, provides the passage, with a filter element therein to prevent bacterial incursion within the eye and to regulate aqueous humor flow. The filter may be replaceable, if necessary, by vacuum removal. The invention includes an installation device for cutting the slit and a device for gaping open the slit and for guiding and locking the stent into proper placement.

8 Claims, 2 Drawing Sheets

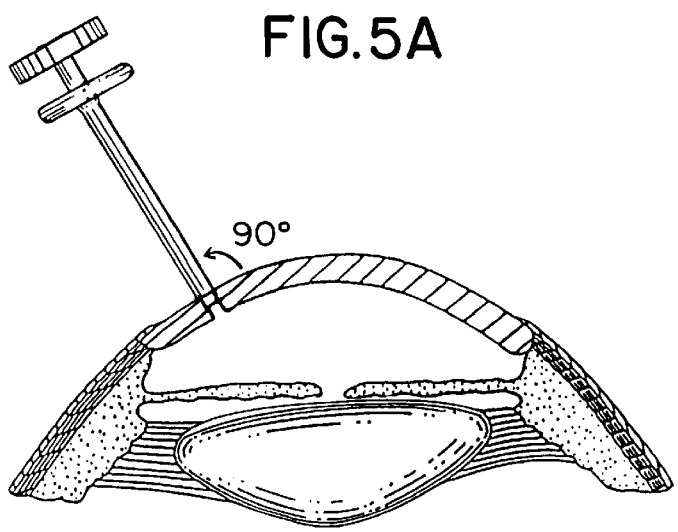
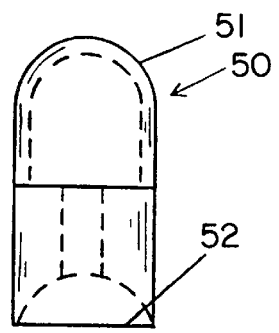
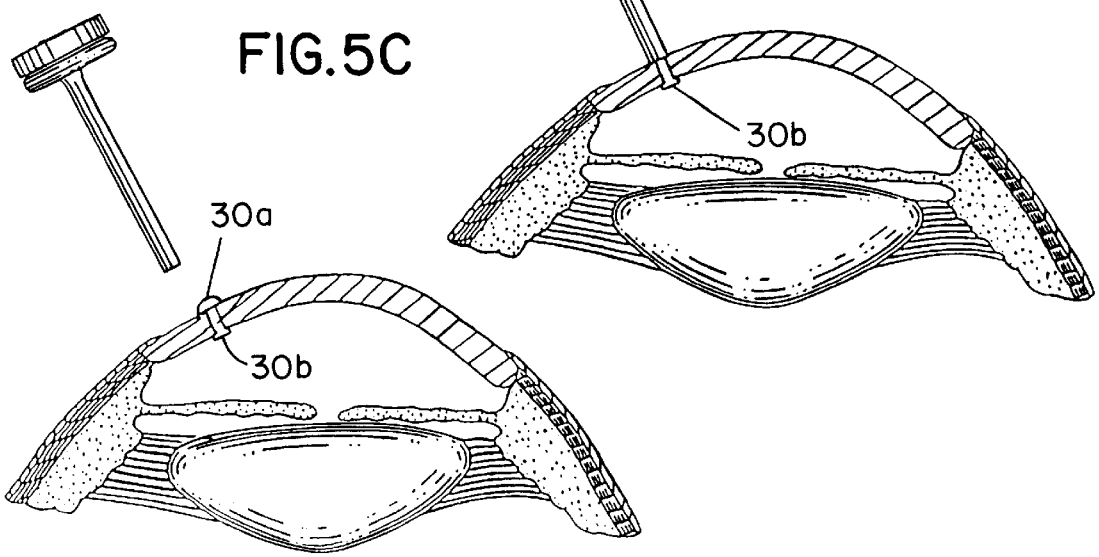

TREATMENT OF GLAUCOMA

FIELD OF THE INVENTION

This invention relates to methods and devices utilized in the treatment of glaucoma for the relief of internal eye pressure, and particularly to drainage stents for relieving such pressure.

BACKGROUND OF THE INVENTION

Glaucoma, an abnormal condition of the eye, results from the build-up of internal fluid pressure, within the eye, which can eventually lead to damage of the optic nerve and ultimately to loss of vision and even blindness. Relief of the excess pressure is effected by various types of treatments. These treatments range from drugs to surgical procedures and implants which are used to relieve the excess pressure.

Among the devices, or implants, for the relief of such pressure, are stents which are implanted within the eye. The stents are placed in a position whereby they serve to relieve internal eye pressure by permitting aqueous humor to flow from the anterior chamber through the sclera and thereafter draining of the fluid from a conjunctive bleb over the sclera into the tear film. However, a common problem with this procedure is that the pouch or filtration bleb is likely to close from scar tissue formation.

Another problem is the relative inaccessibility of many of such implanted stents for removal and/or replacement.

It is therefore an object of the present invention to provide a procedure and a device for use in such procedure which permits direct drainage of the aqueous humor to the tear film, without a filtration bleb, and also without thereby increasing the incidence of bacterial infection.

It is a further object of the present invention to provide a drainage device for direct drainage of aqueous humor to the tear film, to relieve excess eye pressure, and having means for preventing bacterial infection of the eye.

It is yet another object of the present invention to provide such drainage device whereby it and bacterial prevention filtration means therein are removable for replacement thereof.

It is still yet another object of the present invention to provide an insertion device to facilitate the accurate placement of the drainage device.

These and other objects, features and advantages of the present invention will become more evident from the following discussion and drawings in which:

SHORT DESCRIPTION OF THE DRAWINGS

Figure 4A:
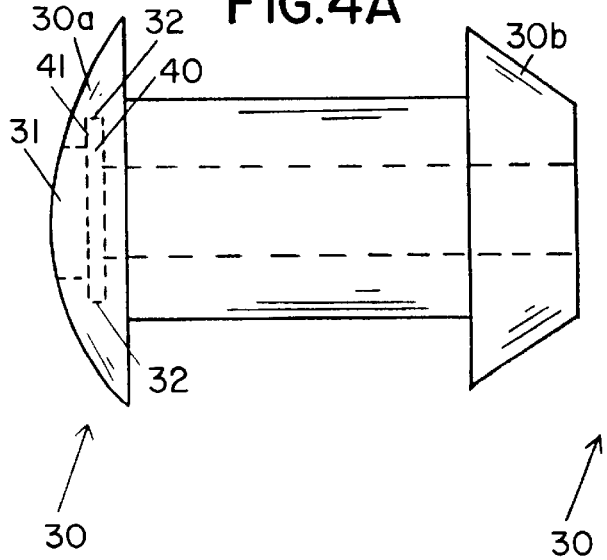
FIGS. 4a and 4b depict the filter element which is inserted in the stent in replaceable and non-replaceable manners respectively.

FIGS. 5a–c sequentially show the placement operation and the final position of the stent in an eye; and FIG. 6 depicts a vacuum operated device, with interior shown in phantom, for removal and replacement of the filter element, as shown in FIG. 4a.

SUMMARY OF THE INVENTION

Generally the present invention comprises a device and a method, using such device, for treatment of glaucoma with relief of excess pressure. The device comprises drainage stent means adapted to be placed in a transcorneal position, to directly connect the anterior chamber and the tear film, for direct fluid drainage and relief of excess pressure. The drainage stent means comprises filtration means capable of preventing passage therethrough of bacteria, while permitting sufficient fluid drainage therethrough, whereby the direct drainage does not result in bacterial infection of the eye. Preferably a microporous filter, such as a millipore filter, with a maximum pore size of 0.2 microns provides the requisite bacterial passage prevention means, while permitting fluid passage therethrough for relief of fluid pressure.

The treatment method comprises the steps of:
a) cutting an incision, preferably a linear incision, of measured depth directly into the cornea of the eye subject to the glaucoma condition;
b) temporarily gaping open the incision with gaping means;
c) positioning drainage stent means within the gaped open incision; and
d) fixing the drainage stent means within the gaped open incision by removal of the gaping means whereby the gaped open incision closes, to engage outer walls of the stent;
to thereby directly connect the anterior chamber and the tear film with drainage means, for direct pressure relief, without a bleb.

The drainage stent means further includes optionally removable filtration means therein, capable of preventing bacterial flow therethrough, and means for the fixed, but removable placement of the stent in a position extending through the cornea. The means for fixed placement preferably comprises end collars which engage the inner and outer surface of the cornea peripheral to the slit, when the insertion means, which gapes open the incision, is removed. Other means include a center positioned ring which engages the cornea and other similar means.

The device of the present invention collectively comprises the stent and an installation device for installation of the stent in the cornea. The installation device comprises an incision device which cuts a controlled depth and size incision in the cornea, without removal of corneal tissue. The installation device further comprises a separate tool having means for temporarily gaping open the incision and for installing the stent through the gaped open incision into fixed placement position. Removal of the tool results in closing of the gaped incision periphery around the stent.

Prior art stent members have not been used in the cornea to effect a direct connection between the anterior chamber and the tear film, primarily since there is a much greater likelihood of detrimental bacterial infection with such direct connection to the tear film. Secondarily, since the cornea is directly involved in the actual vision, as compared to the sclera, direct perforation of the cornea has been avoided. However, in accordance with the present invention, the drainage stent is of minimal size and can accordingly be positioned well off center to obviate any possible problems with vision impairment.

The present invention further comprises an installation method and installation device which reduces tissue stress upon insertion, fixed placement, and removal of the stent in the cornea. In addition, in order to prevent infection because of the direct exposure to the tear film, the stent contains bacterial prevention filtration means, which may be optionally replaceable. The device comprises an initial cutting tool for incision of a controlled size slit in the cornea and an insertion tool which can also be used as a removal tool for both insertion placement of the stent and the removal thereof.

The insertion tool comprises means for temporarily gaping the controlled size slit to an extent sufficient for facilitated insertion of the stent into the gap and into its holding position. Removal of the insertion tool results in closing of the gap with the cornea tissue, adjacent the slit, enclosingly engaging the stent. With an optional replaceable filter, a vacuum device is utilized to pull the filter out and to also replace it.

DETAILED DESCRIPTION OF THE INVENTION

In accordance with the present invention, the cornea of an eye subject to glaucoma conditions, is pre-slit to the anterior chamber thereof, with a specially constructed tool which serves to make the slit for the insertion of the stent. In accordance with a preferred embodiment of the present invention, the stent means comprises a hollow tube member with integral collars or flanges at both ends thereof, adapted to engage the inner and outer surfaces of the cornea in preventing removal of the stent from its transcorneal position.

The length of the stent is sufficient to snugly, though not tightly, permit engagement of the collar members with the inner and outer surfaces of the cornea and the stent is comprised of an ophthalmically acceptable polymeric material having structural integrity. Bacterial prevention filtration means, such as a microperforated disc, a porous cellulosic material plug, and the like, all of appropriate pore size, is positioned within or directly adjacent the hollow of the stent in the path of the fluid flow. In such position, the filtration means serves the dual function of permitting pressure relief by flow of excess fluid to the tear film at a controlled rate, and more importantly, prevents inflow of possibly infectious material, which may occur despite the outward pressure gradient, from the tear film. The filter member may be cemented in place or removably inserted within the stent whereby it can be replaced, as needed.

For facilitated removal and replacement, the filter is positioned at the portion of the stent adjacent the exterior surface of the cornea and is supported by the collar or flange resting on the exterior surface. Support means are provided on the collar or flange which cooperate with a portion of the filter structure to prevent the aqueous humor pressure, passing through the stent, from dislodging the filter. Such support means are however disengageable for removal of the filter for replacement purposes.

With use of a microperforated disc, the perforations are preferably effected by laser cutting, and the number and size thereof is primarily related to bacteria flow prevention and secondarily to the degree of pressure to be relieved. Thus, with changes in the glaucoma condition, microperforated discs of varying perforations can be readily replaced one for the other as required.

DETAILED DESCRIPTION OF THE DRAWINGS AND THE PREFERRED EMBODIMENT

Figure 1:
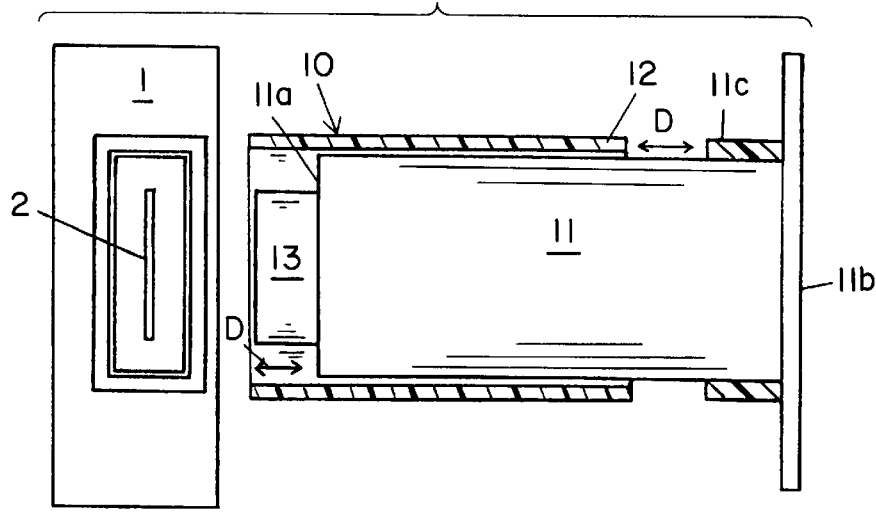
FIG. 1 is a side view of the incision tool used during the installation procedure of the drainage device of the present invention, with a schematic view of an incision.

With reference to the drawings, in FIG. 1, an incision tool 10 is shown, in schematic open cross-section, with a plunger 11, within casing 12. End 11a of the plunger 11 terminates in blade member 13 and the other end 11b is used for actuation. In operation, casing 12 is brought to rest on cornea 1, plunger end 11b is depressed and slanted blade member 13 cuts slit 2 into the surface of the cornea. Casing 12 provides an arrest against stop element 11c of the plunger, whereby blade travel is controlled to a distance D, just sufficient to provide a transcorneal incision. Withdrawal of the plunger 11, removes the blade from the formed slit 2 and the incision tool is removed. Length of the blade and slit 2, is about 2.5 mm. With the incision made in this fashion, minimal corneal tissue is removed.

Figure 2:
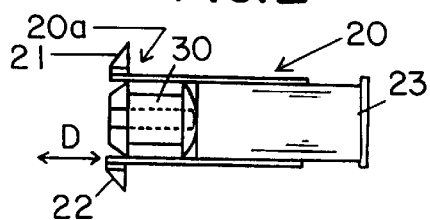
FIG. 2 is a sectioned side view of the installation tool used to install the stent drainage device of the present invention, with the stent shown in side view.
Figure 3:
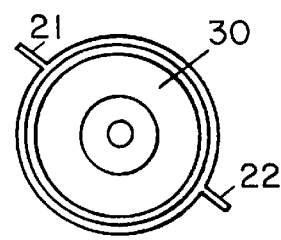
FIG. 3 is a view taken along line 3—3 of FIG. 2.

Immediately thereafter, installation tool 20, shown in schematic open cross-section in FIG. 2, with stent 30 loaded therein, is initially partially inserted into slit 2. Radially extending wings 21 and 22, positioned at the forward end 20a of the installation tool 20 and set 180° apart from each, are fitted into opposite ends of slit 2 and are rotated within the slit 2, by rotation of the tool 20, by 90° in any direction, thereby causing wings 21 and 22 to gape open slit 2 into an elliptical shape. Wings 21 and 22 are triangular in shape in order to facilitate a guided, gradual insertion thereof within the terminal ends of the slit 2. The wings are further provided with barb members 21' and 22', respectively, to permit the wings to more firmly engage and hold the walls of the cornea, without slippage, during insertion and rotation for gaping. Plunger 23 of tool 20 is then depressed whereby plunger end 23a, engaged with an end of stent 30, pushes it (for a distance D) through gaped open slit 2 into the transcorneal position, indicated by flush positioning of outer flange or collar 30a with outer corneal surface 1a. The installation tool 20 is then return rotated by 90° and removed. As shown in the installation sequence of FIGS. 5a–c, insertion of wings 21 and 22 partially within the incision, and rotation, effects the gaping operation (FIG. 5a); depression of plunger 21 causes the stent to be positioned with collar 30b being shown as engaging the inner surface of the cornea (FIG. 5b); and removal of installation tool 20 of the installation tool 20, results in the tight engagement of the corneal stroma with the sides of stent 30 and collars 30a and 30b with the outer and inner surfaces of the cornea 1 respectively (FIG. 5c).

Figure 4B:
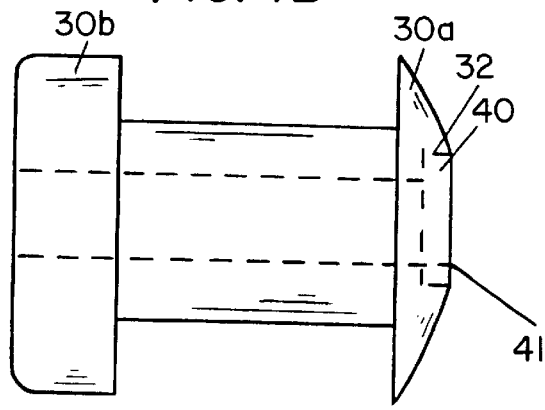

Filter member 40, shown most clearly in FIG. 4a, fits into through-aperture 31 of stent 30 and is held therein by means of flange 41 of the filter member, being inserted into peripheral recess 32 in collar 30a. The filter member may be an elongated porous, fibrous material in the form of a plug with an end holding flange. Alternatively the filter member may a microporous disc such as a millipore filter 40, which fits entirely within the recess area 32 and is removably held by holding flange 33. Alternatively, as shown in FIG. 4b, the filter member 40 may be cemented in place for relatively permanent placement. As shown in FIG. 6 a filter replacement device 50 has an end 52 conformed to the exposed surface of filter 40. Thereafter, a partial vacuum is effected through the device 50 by compression of a flexible end 51 to pull the filter out of place from the stent. A replacement filter 40 is then placed on the device end 52 and held thereon by the vacuum which vacuum is released when the new filter is properly positioned in the stent. The main body of stent 30 has an appropriate diameter of about 0.85 mm and a collar diameter of about 1.45 mm. Suitable dimensions for the stent member 30 are a total length of about 1.3 mm with a stent length between collars 30a and 30b of about 1.0 mm (about matched to a typical cornea thickness).

In performing the incision and installation procedures, topical anesthetic drops are applied to the corneal region (e.g., peribulbar Lidocaine). Correct positioning of the stent implant is indicated by a bead of aqueous humor which wells from the cap of the stent implant.

It is understood that the above description, drawings and preferred embodiment are only exemplary of the present invention and that changes may be made to the various operations and structures of the stent and installation devices without departing from the scope of the present invention as defined in the following claims.

What is claimed is:

1. A system for the insertion of a stent through the cornea of an eye, said system directly connecting an anterior chamber of the eye, having aqueous humor therein, to a tear film, for direct pressure relief from a glaucoma condition, said system comprising means for cutting a linear incision in the cornea, means for temporarily gaping open said linear incision, and a separate means for installing the stent within the linear incision while said incision is gaped open by the means for temporarily gaping open the linear incision, whereby when the stent is installed, the stent provides a passage for a direct connection between anterior chamber and the tear film through the cornea.

2. The system of claim 1, wherein the cutting means further comprises a collar whereby the incision is of a measured depth only sufficient to reach an interior surface of the cornea.

3. The system of claim 2, wherein the gaping means and installing means are integrated whereby gaping open of the incision with the gaping means aligns the stent for insertion within the gaped open incision.

4. The system of claim 3, wherein the gaping means comprise separated wing members extending in opposite directions, sized to fit within said incision adjacent walls of the incision, wherein rotation of the wing members effects the incision.

5. The system of claim 4, wherein a plunger is aligned in a space between the wing members, said plunger being adapted to engage an end of a stent placed in the space between the wing members whereby plunging activation of the plunger pushes the stent between the wing members into a position to connect the anterior chamber of the eye and the tear film.

6. A drainage stent for relief of excess pressure in an eye, resulting from a glaucoma condition, said stent being adapted to be placed through a cornea of the eye, in a transcorneal position, to directly connect an anterior chamber of the eye and a tear film on the outer surface of the cornea for direct fluid drainage from the anterior chamber and relief of excess pressure, said drainage stent comprising filtration means capable of preventing passage therethrough of bacteria, while permitting sufficient fluid drainage therethrough to relieve excess pressure, wherein the stent comprises a hollow tubular member having a pair of collar elements for respective engagement with an inner and outer surface of the cornea, and wherein the filter is positioned to block access of bacteria through the hollow tubular member.

7. The drainage stent of claim 6 wherein the filtration means comprises a microporous filter with a maximum pore size of 0.2 microns.

8. The drainage stent of claim 7, wherein the microporous filter is removable from the stent for replacement thereof.

* * * * *